United States Patent [19]
Lochhead et al.

[11] Patent Number: 4,686,254
[45] Date of Patent: Aug. 11, 1987

[54] SUSPENSION COMPOSITION FOR AQUEOUS SURFACTANT SYSTEMS

[75] Inventors: Robert Y. Lochhead, Avon Lake; Debra S. S. Warfield, Fairview Park, both of Ohio

[73] Assignee: The B. F. Goodrich Company, Akron, Ohio

[21] Appl. No.: 762,175

[22] Filed: Aug. 5, 1985

[51] Int. Cl.$^4$ ................................................ C08K 5/34
[52] U.S. Cl. ................................ 524/99; 424/DIG. 4; 424/70; 524/156; 524/157; 524/158; 524/551; 524/555; 524/556; 526/317
[58] Field of Search ................. 524/99, 156, 157, 158, 524/551, 555, 556; 526/317; 424/70, DIG. 4

[56] References Cited

U.S. PATENT DOCUMENTS 4,420,596 12/1983 Lochhead et al. ................ 526/212
4,509,949 4/1985 Huang et al. ................ 526/317 X
4,557,928 12/1985 Glover ................................ 424/70

FOREIGN PATENT DOCUMENTS 2122214 11/1985 United Kingdom .

OTHER PUBLICATIONS

CA 103(14):109766a, "Dispersions of Antifungal Agents and Antifungal Hair Treatment Compositions'-'-Kao Corp.; 1985.
CA 100(10):70383j, "Washing Composition" Unilerer N. V.; 1983.
CA 99(4):28016c, "Antidandruff Cream Rinse Conditioner" Amway Corp.; 1983.
CA 94(18):145178q, "Antimicrobial Shampoo" Mitsubishi Petro Chemical Co., Ltd.; 1980.
CA 97(22):188095q, "Shampoos Containing 2-Pyridinethiol 1-Oxide Salts; Johnson Co., Ltd.; 1982.

Primary Examiner—Joseph L. Schofer
Assistant Examiner—J. M. Reddick
Attorney, Agent, or Firm—George A. Kap; Alan A. Csontos

[57] ABSTRACT

This invention is directed to stable compositions comprising an anionic surfactant and a salt-stable copolymer; and to suspension compositions comprising a surfactant, a salt-stable copolymer, and normally incompatible ingredient such as an anti-dandruff agent, the polymer being used in an amount to sufficiently thicken the composition and to permanently suspend the ingredient.

6 Claims, No Drawings

SUSPENSION COMPOSITION FOR AQUEOUS SURFACTANT SYSTEMS

BACKGROUND OF THE INVENTION

For the past quarter of a century, crosslinked homopolymers of acrylic acid have provided a route to permanent suspension of insoluble or incompatible ingredients in water-based systems. Many modern emulsion products rely on such polymers of acrylic acid to provide excellent stability against creaming or coalescence during storage and to allow easy flow of the product from its container during application.

The homopolymers of acrylic acid should not be regarded solely as a means of increasing viscosity of a formulation. An increase in viscosity alone is not sufficient to provide permanent suspension of a dispersed phase. Stokes' Law tells us that merely increasing viscosity will delay but not stop separation or sedimentation of particles or droplets suspended in a liquid. This assumes, of course, that the particles are too large to be suspended by Brownian motion.

Systems thickened with homopolymers of acrylic acid display plastic rheology. Materials that exhibit plastic flow characteristics will flow only after the applied shearing stress exceeds a critical minimum value. This minimum shearing stress is designated as yield value. At stresses below the yield value, the system displays the rheology of a solid whereas at shearing stresses above the yield value, the system exhibits liquid-like rheology. This explains the ability of the polymers of acrylic acid to suspend insoluble particles in systems at rest but to flow easily once the yield value is exceeded.

Although homopolymers of acrylic acid have been used for many years to suspend insoluble or incompatible ingredients in water-based systems, such polymers are not compatible with anionic surfactants and do not effectively suspend certain ingredients in the manufacture of personal care products.

SUMMARY OF THE INVENTION

This invention is directed to suspension compositions comprising at least one anionic surfactant and a copolymer of a carboxylic acid and to suspension compositions comprising at least one anionic surfactant, a copolymer of a carboxylic acid, and an incompatible ingredient. The copolymer is an effective thickener, especially in neutralized or salt form, in applications where high ionic environments are encountered and is characterized by the presence of a small amount of at least one acrylic ester monomer. Such copolymers are compatible with anionic surfactants, they can effectively suspend certain incompatible ingredients that other similar materials cannot, and their use in a formulation can substantially reduce amount of a surfactant needed, thus resulting in a milder formulation. Amount of such copolymers should be sufficient for effective suspension of incompatible ingredients.

DETAILED DESCRIPTION OF THE INVENTION

The salt-stable carboxylic acid copolymers described herein are well known. They are described in the Huang et al U.S. Pat. No. 4,509,949, assigned to the assignee of the subject invention, which is incorporated herein in its entirety. Such polymers are more stable in ionic environment than their counterparts which are devoid of the small amount of a long chain alkyl acrylate. For this reason, such copolymers are generally referred to herein as being salt-stable.

The carboxylic acids useful in the production of the salt-stable copolymers referred to herein are the olefinically unsaturated carboxylic acids containing at least one activated carbon-to-carbon olefinic double bond and at least one carboxyl group. The olefinic double bond readily functions in polymerization because of its presence in the monomer molecule either in the alpha-beta position with respect to a carboxyl group or as a part of a terminal methylene grouping, i.e., $CH_2<$. Olefinically unsaturated acids in this group include acrylic acids typified by the acrylic acid itself, methacrylic acid, ethacrylic acid, alpha-chloroacrylic acid, alpha-cyano acrylic acid, beta methylacrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid, itaconic acid, citraconic acid, mesaconic acid, glutaconic acid, aconitic acid, maleic acid, fumaric acid, and tricarboxy ethylene. As used herein, the term carboxylic acid includes anhydrides as well as the polycarboxylic acids and those acid anhydrides, such as maleic anhydride, wherein the anhydride group is formed by the elimination of one molecule of water from two carboxyl groups located on the same polycarboxylic acid molecule.

The preferred carboxylic acids are the acrylic acids having the general structure $$CH_2=\underset{\underset{R^1}{|}}{C}-COOH$$

wherein $R^1$ is a substituent selected from the class consisting of hydrogen, halogen, and the cyanogen ($-C\equiv N$) groups, monovalent alkyl radicals of 1 to 4 carbons, monovalent aryl radicals of 6 to 14 carbons, monovalent aralkyl radicals of 7 to 14 carbons, monovalent alkaryl radicals of 7 to 12 carbons, and monovalent cycloaliphatic radicals of 4 to 8 carbon atoms. Of this class, acrylic, methacrylic, and ethacrylic acids are most preferred. Another useful carboxylic monomer is maleic anhydride or the acid.

The amount of carboxylic acid used is from about 95 to about 99 weight percent of the total monomers used. More preferably, the range is from about 96 to about 98 weight percent.

Suitable acrylic ester monomers for purposes herein are defined as follows:

$$CH_2=\underset{\underset{R^2}{|}}{C}-\underset{\underset{}{\overset{O}{\|}}}{C}-O-R^3$$

where R is hydrogen, methyl or ethyl group and where $R^3$ is an alkyl group having 10 to 30 carbon atoms, preferably 12 to 22 carbon atoms. Representative acrylic esters include decyl acrylate, isodecyl acrylate, lauryl acrylate, dodecyl acrylate, stearyl acrylate, and the corresponding methacrylates. Mixtures of two or more of the long chain acrylic esters can be successfully polymerized with one or more of the carboxylic acids.

Amount of the acrylic ester monomer in all of the monomers that are polymerized is 1 to 5 weight percent, preferably 2 to 4 weight percent. The monomers that are polymerized to produce the carboxylic acid polymer include one or more unsaturated carboxylic acid monomer in a major proportion and one or more acrylic ester monomer in a minor proportion, as defined herein.

The salt-stable carboxylic acid copolymers described herein are crosslinked with a polyfunctional vinylidene monomer containing at least two terminal $CH_2=C<$ groups. Particularly useful crosslinking monomers for use herein are polyalkenyl polyethers having more than one alkenyl ether group per molecule, and the most useful monomers have alkenyl groups in which an olefinic double bond is attached to a terminal methylene group, i.e., $CH_2=C<$. Such monomers can be prepared by the etherification of a polyhydric alcohol containing at least four carbon atoms and at least two hydroxyl groups. Products of such reactions are complex mixtures of polyethers with varying number of ether groups. It is preferred to use polyethers containing an average of two or more alkenyl ether groups per molecule. Other crosslinking monomers can also be used. Allyl pentaerythritol, trimethylolpropane diallylether, and allyl sucrose are exceptional crosslinking monomers for purposes herein.

Amount of a crosslinking monomer used in the polymerization of the monomers defined herein can vary from 0.1 to 1 weight percent, based on the weight of the total monomer mixture of one or more of the carboxylic acid monomers and one or more of the acrylic ester monomers. In a preferred embodiment, this amount can be in the range of about 0.1 to 0.6 weight percent.

Other vinylidene monomers can be used in place of the carboxylic acid in small amounts so long as the basic properties of the thickening agents are not adversely affected. Examples include acrylonitrile, methacrylonitrile, acrylamide, methacrylamide, styrene, vinyl toluene, vinyl methyl ether, vinyl ethyl ketone, butadiene, vinyl acetate, methyl acrylate, butyl acrylate, cyanopropyl acrylate, methoxyethyl acrylate, chloroethyl acrylate, vinyl chloride, vinylidene chloride, esters of maleic and fumaric acid, bis($\beta$-chloroethyl) vinyl phosphonates, and the like monomers that are known to those skilled in the art.

The carboxyl acid polymers described herein have molecular weights greater than about 500 to as high as several million. In a preferred embodiment, molecular weight of such polymers is in the range of about 100,000 to 5 million.

Polymerization of the monomers is usually carried out in the presence of a free radical catalyst in an inert atmosphere under pressure, with proper agitation. The process can be batch or continuous. Polymerization temperature can be varied from 0° to 125° C. and polymerization at 25° to 90° C. in presence of a free radical catalyst is generally effective in obtaining polymer yields of 75 to 100%. The monomers can be batch charged or charged continuously during the course of polymerization, or in any other manner conventionally used. Typical free radical forming catalysts include peroxygen compounds such as sodium, potassium and ammonium persulfates, caprylyl peroxide, benzoyl peroxide, hydrogen peroxide, pelargonyl peroxide, cumene hydroperoxides, tertiary butyl diperphthalate, tertiary butyl perbenzoate, sodium peracetate, di(2-ethylhexyl)-peroxydicarbonate, and the like, as well as azo catalysts such as azodiisobutyryl nitrile. Other catalysts utilized are the so-called "redox" type of catalyst and the heavy-metal activated catalyst systems. Ultra-violet light may also be used as a source of free radicals. Some systems polymerize solely by heat, but catalysts provide better control.

Polymerization of the monomers is conducted in a solvent or an inert organic liquid in which the monomers are soluble but in which the resulting polymer is insoluble. The polymerization medium can be a mixture of suitable organic liquids. The product is preferably obtained as a very fine friable or fluffy precipitate. Typical solvents include hydrocarbons containing 6 to 8 carbon atoms such as benzene, tetralin, hexane, heptane, cyclohexane as well as carbon tetrachloride, chloroform, trichloroethylene, methyl chloride, ethyl chloride, and methylene chloride; chlorofluoroalkanes such as chlorofluoromethane and chlorofluoroethane containing at least 4 halogen atoms; esters such as methyl acetate and ethyl acetate; alcohols including methanol, ethanol, butanol, and the like. Amount of organic medium used normally will be in excess of the monomers to be polymerized and the proportion may vary from at least 1 weight percent of monomers and 99 weight percent organic medium up to about 50 weight percent monomers and 50 weight percent medium.

In the presence of anionic surfactants, the salt-stable copolymers disclosed herein provide greater thickening efficiency and yield values than the conventional homopolyacrylic acids. Viscosity and yield value of anionic surfactant systems thickened with the copolymers disclosed herein are generally on the order of 50% higher than with the conventional homopolyacrylic acids, which is expected in view of the modification involved.

The anionic organic surfactants are selected from alkali metal alkyl sulfates containing 8 to 22 carbon atoms in the alkyl group, alkylbenzene sulfonates containing 10 to 20 carbon atoms in the alkyl group, alkali metal glyceryl ether sulfonates, alkali metal fatty acid monoglyceride sulfates and sulfonates, and other anionic surfactants. More specifically, anionic surfactants are selected from water soluble salts and alkali metal salts of organic sulfuric acid reaction products having in their molecular structure an alkyl radical of about 8 to 22 carbon atoms and a radical selected from sulfonic acid and sulfuric acid ester radicals. Included in the term alkyl is the alkyl portion of higher acyl radicals. Important examples of anionic surfactants are the sodium or potassium alkyl sulfates, especially those obtained by sulfating the higher alcohols of $C_8$ to $C_{18}$ carbon atoms produced by splitting the glycerides of tallow or coconut oil, and sodium or potassium alkyl benzenesulfonates, in which the alkyl group contains about 9 to 15 carbon atoms.

Other examples of alkali metal alkylbenzene sulfonates are those in which the alkyl radical is a straight or branched chain aliphatic radical containing about 10 to 20 carbon atoms. Sodium alkyl glyceryl ether sulfonates, especially those ethers of the higher alcohols derived from tallow and coconut oil. Sodium coconut oil fatty acid monoglyceride sulfates and sulfonates. Sodium or potassium salts of sulfuric acid esters of the reaction product of one mole of a higher fatty alcohol and about 1 to 6 moles of ethylene oxide. Sodium or potassium salts of alkylphenol ethylene oxide ether sulfate with about 1 to 10 units of ethylene oxide per molecule in which the alkyl radicals contain about 9 to 12 carbon atoms. The reaction product of fatty acids esterified with isethionic acid and neutralized with sodium hydroxide where, for example, the fatty acids are derived from coconut oil. Sodium or potassium salts of fatty acid amide of a methyl tauride in which the fatty acids, for example, are derived from coconut oil. Sulfonated polycarboxylic acids derived from pyrolyzed calcium citrate.

Of particular interest herein are the water-soluble anionic surfactants such as alkali metal alkyl sulfates containing 8 to 22 carbon atoms in the alkyl group, alkanol-amine alkyl sulfates containing 1 to 6 carbon atoms in the alkanol group and 8 to 22 carbon atoms in the alkyl group, ammonium alkyl sulfates containing 8 to 22 carbon atoms in the alkyl group, and alkali metal alkyl ether sulfates containing 8 to 22 carbon atoms in the alkyl group. Specific examples of such anionic surfactants are sodium lauryl ether sulfate, ammonium lauryl sulfate, and triethanolamine lauryl sulfate.

The salt-stable copolymers of acrylic acids described herein are also particularly effective in suspending incompatible materials in water-based systems, such as anti-dandruff agents, pearlizing agents, silicone oil, glitter, etc. Such agents are used at a level of about 0.1 to 6 weight percent, based on the weight of the formulations. The anti-dandruff agents used in commercial products include selenium sulfide, colloidal sulfur, and compounds of pyrithione, especially zinc pyrithione.

In connection with suspension of incompatible ingredients, yield value of a system becomes important since it is an indication of whether a system can maintain suspended an incompatible ingredient. The yield value can be approximated by measuring Brookfield Yield Value (BYV) using a Brookfield RVT viscometer, as follows:

$$BYV = \frac{\text{apparent viscosity at 0.5 rpm} - \text{apparent viscosity at 1 rpm}}{100}$$

For systems containing insoluble particles or droplets, stability against separation can be calculated from the Brookfield Yield Value. Therefore, the minimum BYV for permanent suspension can be calculated as follows:

$$BYV = [23.6R(D-Do)g]^{\frac{1}{3}}$$

where
R = particle radius in cm.
D = density of particle in g/cc
D = density of medium in g/cc
g = acceleration due to gravity in cm/sec$^2$ It has been determined that a Brookfield Yield Value of about 100 is required to suspend zinc pyrithione in the shampoo system described.

Zinc pyrithione is a well known anti-dandruff agent in shampoos. In order to suspend it in a shampoo medium, various systems have been tried with dubious results. For instance, one suspending system uses magnesium aluminum sulfate in conjunction with hydroxy propyl methyl cellulose which, apparently, is not very effective since it is necessary to shake the shampoo composition before use. This implies that zinc pyrithione settles and requires agitation to be redispersed. Another composition relies on the use of a cationic polymer/anionic surfactant complex to suspend zinc pyrithione.

The commercial anti-dandruff shampoo which uses zinc pyrithione as the anti-dandruff agent includes the following significant components: triethanolamine lauryl sulfate (TEALS) anionic surfactant, cocamide monoethanolamide (MEA) foam booster, magnesium aluminum silicate and hydroxy propyl methyl cellulose as a thickener and a suspending combination, and of course, zinc pyrithione as the anti-dandruff agent. Viscosity phase diagrams were prepared for the prior art samples varying in surfactant concentration from 1 to 25%, with the thickener/suspension agent concentration varying from 0.5 to 3%, with the foam booster to surfactant ratio of 1:10 and 1:5, and with the ratio of magnesium aluminum silicate to hydroxy propyl methyl cellulose (thickener/suspension agent) of about 2:1. Data was obtained for homogenized and non-homogenized systems. Comparison was also made by preparing samples with the herein-described salt-stable polymers of acrylic acid and related polyacrylic acids.

Brookfield yield value phase diagrams could not be prepared for the system containing TEALS surfactant, cocamide MEA foam booster and magnesium aluminum silicate ahd hydroxy propyl methyl cellulose thickener/suspension agent. Such systems have a negligible Brookfield yield value which means that magnesium aluminum silicate and hydroxy propyl methyl cellulose do not suspend zinc pyrithione successfully. This is consistent with instructions on products containing such systems to shake same in order to redisperse zinc pyrithione. Homogenizing the samples nor increasing the foam booster to surfactant ratio from 1:10 to 1:5 did not improve performance of the prior art systems. Furthermore, viscosity for all systems containing the prior art thickener/suspension agent increased with increasing surfactant concentration for a given level of the agent.

Comparison samples were also prepared by replacing the prior art thickener/suspending agent, i.e., magnesium aluminum silicate and hydroxy propyl methyl cellulose, with the salt-stable polymer described herein. In these samples, zinc pyrithione was effectively suspended by the copolymer of acrylic acid used in amount of 0.5% by weight whereas 1% magnesium aluminum silicate and 0.5% hydroxy propyl methyl cellulose was ineffective in maintaining a stable suspension. Further evaluations confirmed that such copolymers can suspend zinc pyrithione in such systems at ambient and at elevated temperatures and at freeze-thaw conditions for over six months as long as the suspension or the system has a Brookfield yield value of about 100 and above.

It is important to note that in the system using the prior ar thickener/suspension agent of magnesium aluminum silicate and hydroxy propyl methyl cellulose, an increase in cocamide MEA foam booster causes viscosity to increase at all levels of surfactant and thickener/suspension agent. This shows that rheology of the cocamide MEA dominates the rheology of the thickener/suspension agent. This is not the case in the systems containing the salt-stable polymer. In the salt-stable polymer systems, an increase in the ratio of foam booster to surfactant causes viscosity of the systems to increase at low levels of surfactant and the salt-stable polymer but this increase diminishes as the surfactant level is increased. This shows that rheology of the salt-stable polymer, not the foam booster, dominates the system.

It should be now apparent that shampoos formulated with salt-stable polymers have advantages not realized by the prior art shampoos. The fact that the salt-stable polymer can effectively suspend incompatible ingredients makes them more convenient for consumers to use. It is well known that most anti-dandruff shampoos have to be shaken before use to blend or redisperse their dandruff-fighting ingredients. However, since the salt-stable polymers permanently suspend incompatible ingredients, the shampoo need not be shaken.

For reasons discussed hereafter, shampoos and other personal care products formulated with the salt-stable copolymers, can be milder to the scalp or skin. In the past, such products as shampoos, had to have high levels of detergents to maintain stability. These high levels of detergents could irritate the skin, increasing dryness and flakiness—the conditions the anti-dandruff shampoos and similar products are expected to alleviate. The products formulated with salt-stable copolymers can be prepared with a lesser amount of detergents without loosing their cleansing properties since prior art shampoos used a higher level of detergent than was required for cleansing. This also leads to a reduction in the manufacturing cost since the use of salt-stable polymers can reduce the amount of detergent needed by as much as one half and generally by at least 10%. Stated differently, in a system containing a salt-stable polymer, viscosity decreases with increasing detergent concentration for a given level of salt-stable polymer. This, of course, can lead to the use of a lesser amount of detergent which will lead to a lower cost and less irritability since detergents are purportedly irritants.

Presented below is a typical anti-dandruff shampoo formulation using conventional thickeners and suspending agents to suspend the anti-dandruff ingredient zinc pyrithione. Presented alongside for comparison purposes is a suggested anti-dandruff shampoo formulation with a salt-stable polymer.

| Ingredient | Conventional Shampoo | Shampoo with S—S Copolymer |
|---|---|---|
| Demineralized Water | 62.26% | to 100% |
| Mg—Al Silicate | 1.00 | — |
| Hydroxy Propyl Methyl Cellulose | 0.50 | — |
| TEA Lauryl Sulfate | 25.00 | 10.0 |
| TEA (99%) | 1.00 | 1.0 |
| Salt-Stable Polymer | — | 0.5 |
| Cocamide Monoethanolamide | 5.50 | 2.0 |
| Zinc Pyrithione (48%) | 4.20 | 2.0 |
| Colors | 0.14 | 0.1 |
| Perfume | 0.40 | 0.4 |
| | 100.00 wt. % | 100.00 wt. % |

TEA used above, is a contraction for triethanol amine. The TEA lauryl sulfate was a 40% solution of the surfactant in water, and was the main surfactant. TEA itself was a 99% solution and was used to adjust pH of the formulation. Cocamide monoethanolamide was a foam booster whereas zinc pyrithione, used as a 48% dispersion in water, was the anti-dandruff agent. Zinc pyrithione itself is a powder that produces opaque products. Magnesium-aluminum silicate and hydroxy propyl methyl cellulose are the prior art thickener/suspension agent which are replaced by the salt-stable polymer in the new anti-dandruff shampoo formulation.

The above comparison clearly shows the drastic reduction in detergent that can accompany the use of a salt-stable polymer in place of the prior art thickener/suspension agent. It is pointed out that, although the new formulation contains a substantially smaller amount of the detergent, the cleansing performance is not diminished thereby and other advantages are realized as already noted.

The anti-dandruff shampoos with the salt-stable polymer can have formulations defined as follows:

| Ingredient | Wt. Percent |
|---|---|
| Water | 45–80 |
| Salt-Stable Polymer | 0.3–3 |
| Surfactant | 5–30 |
| Base for pH Adjustment | 1 |
| Foam Booster | 2–6 |
| Anti-dandruff Agent | 0.5–5 |
| Colors | 0.1–0.2 |
| Perfume | 0.1–1 |
| | 100 wt. % |

The pH adjustment is made using a conventional basic material in order to have the formulation pH of about 5–10, preferable 6–8. Amount of water to be used in preparing the above formulation should be such as to produce a thickened liquid with a viscosity of about 1,000 to 50,000 cps, measured at 20° C.

We claim:

1. Composition containing suspended ingredients therein which are normally incompatible, said composition comprising 5 to 30 weight percent surfactant, 0.1 to 5 weight percent one or more anti-dandruff ingredient(s), 45 to 80 weight percent water, and an effective amount of a polymer to sufficiently thicken said composition and to suspend said ingredient so that it remains suspended, all amounts being based on the weight of the final formulation, said polymer being a polymerization product of 95 to 99 weight percent of one or more carboxylic acid(s), and 5 to 1 weight percent of one or more acrylic esters(s), crosslinked with a small amount of a crosslinking agent selected from polyalkenyl polyetheres having more than one alkenyl ether group per molecule, said carboxylic acid is selected from olefinically unsaturated acids defined as follows:

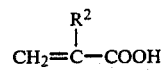

where $R_2$ is selected from hydrogen, halogens, cyanogen group —C≡N, alkyl radicals of 1 to 4 carbon atoms, aryl radicals of 6 to 14 carbon atoms, aralkyl radicals of 7 to 14 carbon atoms, alkaryl radicals 7 to 12, and cycloaliphatic radicals of 4 to 8 carbon atoms; said acrylic ester is defined as follows:

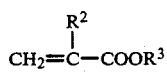

where $R^2$ is defined above in connection with said carboxylic acid and wherein $R^3$ is selected from alkyl groups of 10 to 30 carbon atoms.

2. Composition of claim 1 wherein amount of said polymer is 0.3 to 3 weight percent, wherein said polymer is a polymerization product of 96 to 98 weight percent of one or more of said carboxylic acids and 4 to 2 weight percent of said acrylic esters, and wherein said crosslinking agent is used in an amount of 0.1 to 0.6 weight percent, it is polymerized in said polymer, and is selected from polyalkenyl polyethers of a polyhydric alcohol containing more than one alkenyl ether group per molecule where said polyhydric alocohol contains at least three carbon atoms and at least three hydroxyl groups.

3. Composition of claim 2 wherein $R^2$ is hydrogen or methyl for said carboxylic acid and said acrylic ester, wherein $R^3$ is an alkyl group of 12 to 22 carbon atoms, wherein said crosslinking agent is used in an amount of 0.2 to 0.4 weight percent, and wherein said surfactant is selected from alkyl sulfates containing 8 to 22 carbon atoms in the alkyl group, alkylbenzene sulfonates containing 10 to 20 carbon atoms in the alkyl group, alkali metal glyceryl fatty acid monoglyceride sufates and sulfonates, and mixtures thereof.

4. Composition of claim 2 wherein said carboxylic acid is selected from acrylic acid, methacrylic acid, ethacrylic acid, and mixtures thereof; and wherein said surfactant is anionic and is selected from alkali metal alkyl sufates containing 8 to 22 carbon atoms in the alkyl groups, alkanolamine alkyl sulfates containing 1 to 6 carbon atoms in the alkanol group and 8 to 22 carbon atoms in the alkyl group, ammonium alkyl sulfates containing 8 to 22 carbon atoms in the alkyl group, alkali metal alkyl ether sulfates containing 8 to 22 carbon atoms in the alkyl group, and mixtures thereof.

5. Composition of claim 1 wherein said carboxylic acid is acrylic acid, said acrylic ester is stearyl methacrylate, and said crosslinking agent is selected from alkyl pentaerythritol, trimethylopropane diallylether, allyl sucrose, and mixtures thereof.

6. Composition of claim 5 wherein said incompatible ingredient is selected from zinc pyrithione and said composition has Brookfield yield value of about 100 and greater to permanently suspend zinc pyrithione.

* * * * *